US008888768B2

(12) United States Patent
Babkin et al.

(10) Patent No.: US 8,888,768 B2
(45) Date of Patent: Nov. 18, 2014

(54) CRYOABLATION SYSTEM HAVING DOCKING STATION FOR CHARGING CRYOGEN CONTAINERS AND RELATED METHOD

(75) Inventors: Alexei Babkin, Albuquerque, NM (US); Peter Littrup, Bloomfield Hills, MI (US); William Nydam, Rancho Santa Fe, CA (US); Barron Nydam, Rancho Santa Fe, CA (US)

(73) Assignee: CryoMedix, LLC, San Diego, CA (US)

( * ) Notice: Subject to any disclaimer, the term of this patent is extended or adjusted under 35 U.S.C. 154(b) by 481 days.

(21) Appl. No.: 12/770,572

(22) Filed: Apr. 29, 2010

(65) Prior Publication Data

US 2010/0280507 A1 Nov. 4, 2010

Related U.S. Application Data

(60) Provisional application No. 61/174,132, filed on Apr. 30, 2009.

(51) Int. Cl.
*A61B 18/02* (2006.01)
*A61B 18/00* (2006.01)

(52) U.S. Cl.
CPC ....... *A61B 18/02* (2013.01); *A61B 2018/00214* (2013.01); *A61B 2018/0212* (2013.01); *A61B 2018/0262* (2013.01)
USPC ................................. 606/21; 606/20; 606/23

(58) Field of Classification Search
USPC ............ 606/21–26; 62/45.1, 47.1, 50.1, 54.1, 62/259.3, 292, 293, 529, 530; 607/105
See application file for complete search history.

(56) References Cited

U.S. PATENT DOCUMENTS

| 4,249,923 A | * | 2/1981 | Walda ............................ 62/394 |
| 4,602,628 A | | 7/1986 | Allen, Jr. |
| 4,946,460 A | | 8/1990 | Merry et al. |
| 5,207,674 A | | 5/1993 | Hamilton |

(Continued)

FOREIGN PATENT DOCUMENTS

| CA | 2440777 | 9/2009 |
| GB | 2432875 A | 6/2007 |

(Continued)

OTHER PUBLICATIONS

Patent Abstracts of Japan; JP2003-075004; Cryogenic Apparatus; Atsutoshi Ishikawa; Publication Date: Dec. 3, 2003.

(Continued)

*Primary Examiner* — Ronald Hupczey, Jr.
*Assistant Examiner* — Khadijeh Vahdat
(74) *Attorney, Agent, or Firm* — Convergent Law Group LLP; Rick Batt

(57) ABSTRACT

A cryoablation system includes thermally insulated containers for holding liquid refrigerant. The containers are placed in a docking station that charges the containers with a liquid refrigerant at a cryogenic temperature suitable for carrying out a surgical procedure. The charged containers are detachably connectable with an inlet line of a cryoablation probe. When the cryoprobe is activated, the chilled liquid refrigerant is transported from a delivery container, through the cryoprobe, and to a recovery container. The recovery container is preferably identical in design to the delivery container. The refilled recovery container is then placed in the docking station to charge. In another embodiment, a cartridge includes a delivery container and recovery container combined as a single unit. Methods are also described.

27 Claims, 3 Drawing Sheets

(56) References Cited

U.S. PATENT DOCUMENTS

| | | | |
|---|---|---|---|
| 5,334,181 A | 8/1994 | Rubinsky et al. | |
| 5,520,682 A | 5/1996 | Baust et al. | |
| 5,573,532 A | 11/1996 | Chang et al. | |
| 5,674,218 A | 10/1997 | Rubinsky et al. | |
| 5,733,247 A | 3/1998 | Fallon | |
| 5,787,715 A | 8/1998 | Dobak, III et al. | |
| 5,916,212 A * | 6/1999 | Baust et al. | 606/22 |
| 5,946,920 A | 9/1999 | Clarke | |
| 5,956,958 A | 9/1999 | Dobak, III et al. | |
| 5,978,697 A | 11/1999 | Maytal et al. | |
| 6,074,572 A | 6/2000 | Li et al. | |
| 6,237,355 B1 | 5/2001 | Li | |
| 6,355,029 B1 | 3/2002 | Joye et al. | |
| 6,471,694 B1 | 10/2002 | Kudaravalli et al. | |
| 6,485,422 B1 | 11/2002 | Mikus et al. | |
| 6,530,234 B1 | 3/2003 | Dobak, III et al. | |
| 6,530,946 B1 | 3/2003 | Noda et al. | |
| 6,537,271 B1 | 3/2003 | Murray et al. | |
| 6,551,309 B1 | 4/2003 | LePivert | |
| 6,685,720 B1 | 2/2004 | Wu et al. | |
| 6,726,653 B2 | 4/2004 | Noda et al. | |
| 6,773,408 B1 | 8/2004 | Acker et al. | |
| 6,893,433 B2 | 5/2005 | Lentz | |
| 6,893,653 B2 | 5/2005 | Abraham et al. | |
| 6,904,305 B2 | 6/2005 | Tsekos | |
| 6,972,015 B2 * | 12/2005 | Joye et al. | 606/21 |
| 6,981,382 B2 * | 1/2006 | Lentz et al. | 62/119 |
| 6,984,233 B2 | 1/2006 | Hooven | |
| 7,004,936 B2 | 2/2006 | Ryba et al. | |
| 7,022,120 B2 | 4/2006 | LaFontaine | |
| 7,081,111 B2 | 7/2006 | Svaasand et al. | |
| 7,192,426 B2 | 3/2007 | Baust et al. | |
| 7,220,252 B2 | 5/2007 | Shah | |
| 2002/0032438 A1 * | 3/2002 | Lafontaine | 606/21 |
| 2002/0083717 A1 | 7/2002 | Mullens et al. | |
| 2002/0115989 A1 * | 8/2002 | Abboud et al. | 606/20 |
| 2003/0024250 A1 * | 2/2003 | Haas et al. | 62/3.2 |
| 2003/0220634 A1 | 11/2003 | Ryba et al. | |
| 2005/0182394 A1 * | 8/2005 | Spero et al. | 606/21 |
| 2005/0203505 A1 | 9/2005 | Megerman et al. | |
| 2006/0004349 A1 | 1/2006 | Ryba et al. | |
| 2006/0155268 A1 | 7/2006 | Amir et al. | |
| 2006/0235375 A1 * | 10/2006 | Littrup et al. | 606/21 |
| 2007/0031338 A1 | 2/2007 | Zabinski | |
| 2007/0043342 A1 | 2/2007 | Kleinberger | |
| 2007/0119190 A1 | 5/2007 | Yan | |
| 2007/0277550 A1 | 12/2007 | Li et al. | |
| 2008/0114344 A1 * | 5/2008 | Xiao et al. | 606/20 |
| 2008/0119839 A1 * | 5/2008 | Vancelette | 606/23 |
| 2008/0121759 A1 | 5/2008 | Behrens et al. | |
| 2008/0161784 A1 | 7/2008 | Hogan et al. | |
| 2009/0270851 A1 * | 10/2009 | Babkin et al. | 606/24 |

FOREIGN PATENT DOCUMENTS

| | | |
|---|---|---|
| WO | 2004086936 A2 | 10/2004 |
| WO | 2005081731 A2 | 9/2005 |
| WO | 2007044980 A2 | 4/2007 |

OTHER PUBLICATIONS

Patent Abstracts of Japan; JP2004-275732; Refrigeration Source for Cryoablation Catheter; Ryba et al.; Publication Date: Jul. 10, 2004.
PCT International Search Report and Written Opinion of the International Searching Authority, issued Jan. 26, 2011, Application No. PCT/US2010/033070.

* cited by examiner

CRYOABLATION SYSTEM HAVING DOCKING STATION FOR CHARGING CRYOGEN CONTAINERS AND RELATED METHOD

CROSS-REFERENCE TO RELATED APPLICATIONS

The present application claims the benefit of Provisional Patent Application No. 61/174,132, entitled Single Phase liquid Cooling System (SPLCS) for Cryoablation Treatment, filed Apr. 30, 2009.

BACKGROUND OF THE INVENTION

This invention is directed to cooling systems for performing a cryosurgical procedure. More particularly, the present invention pertains to cooling systems that use thermally insulated cryogen containers that are connectable to a cryoprobe for freezing biological tissues to cryogenic temperatures. The present invention is particularly, but not exclusively, useful for a cooling system wherein a liquid refrigerant remains in a liquid state as it flows through the system between the cryogenic container and the cryoprobe tip.

Various cryoprobes have small shapes and sizes to achieve selective cooling of biological tissues. Cooling is provided from a part of the cryoprobe (e.g., the cryoprobe tip) that will be in direct thermal contact with the target biological tissue to be treated. For many cryogenic treatment applications, temperatures below −90° C. are desirable, but certain applications will be at warmer temperatures up to 0° C.

Various liquid refrigerants such as nitrogen, argon, nitrous oxide, carbon dioxide, various hydro/fluorocarbons, and others have been tried for cryogenic treatment applications. Liquid nitrogen has a very desirable low temperature of approximately −200° C., but when it is introduced into the freezing zone of the cryoprobe, where it is in thermal contact with surrounding warm biological tissues, its temperature increases above the boiling temperature (−196° C.). Thus, it evaporates and expands several hundred-fold in volume at atmospheric pressure, and rapidly absorbs heat from the probe tip. This enormous increase in volume results in a "vapor lock" effect when the mini-needle of the cryoprobe gets "clogged" by the gaseous nitrogen.

Several liquid nitrogen cooling systems have been proposed. For example, improved cryosurgical systems for supplying liquid nitrogen to a cryoprobe tip are disclosed in U.S. Pat. Nos. 5,520,682 and 7,192,426, both of which are issued to Baust et al. Further, a system for the direct and/or indirect delivery of liquid nitrogen to a cryoprobe tip is disclosed in U.S. Pat. No. 5,334,181 which is issued to Rubinsky et al. For these and other similar type systems, cryosurgical practice shows that current cooling systems that are based on the use of liquid nitrogen as a means to cool a miniature cryoprobe tip are not practicably feasible. In large part, this is due to the rapid transition of the liquid nitrogen into the gaseous state followed by an inevitable "vapor lock".

A Single Phase Liquid Cooling System (SPLCS) for performing a cryosurgical procedure with a cryoprobe that maintains a liquid refrigerant in its liquid state as it flows through the system even while in contact with warm biological tissues is described in patent application Ser. No. 12/425,938 to Babkin et al., filed Apr. 17, 2009, and entitled "Method and System for Cryoablation Treatment" and incorporated herein by reference in its entirety. The system described in the Babkin Application avoids the vapor lock problem. However, it describes a sophisticated flowpath from a cryogen source to the cryosurgical device including passage through a cryogenic refrigerator.

Notwithstanding the above, an improved cryosurgical cooling system is still desired.

SUMMARY OF THE INVENTION

A cryoablation system for the treatment of biological tissues with a cryoablation apparatus includes a liquid refrigerant docking station and one or more thermally insulated containers. The thermally insulated containers are adapted to hold the liquid refrigerant and may be placed or installed in the docking station to be charged. Charging may be performed by filling, replenishing, or direct cooling of the liquid refrigerant.

A refrigerator chills liquid refrigerant to a predetermined cryogenic temperature (e.g. less than −100° C.). In one embodiment a Pulse Tube Refrigerator (PTR) provides the cooling energy to chill the refrigerant. This cold liquid refrigerant is then delivered to the thermally insulated cryogenic containers. In this manner each of the containers is replenished or refilled.

In another embodiment the refrigerator includes a refrigerator line and refrigerator element which is inserted into the containers when the containers are docked. The refrigerator element conducts thermal energy to the liquid refrigerant to directly cool it while the liquid is within the containers.

The containers are connectable with a cryoablation apparatus or cryoprobe. A first or delivery container is charged or filled with liquid refrigerant at a predetermined cryogenic temperature. The delivery container is then fluidly connected to the cryoprobe via an inlet line. In one embodiment the inlet line is insulated with a vacuum shell. The inlet line establishes fluid communication between the cryogenic delivery container and the cryoprobe tip section.

The cryoprobe also includes a return line extending proximally from the cryoprobe tip section to a second or empty receiver container. A pump along the flowpath of the liquid refrigerant drives the liquid from the first container, to the probe tip section, and to the second or empty container.

The shaft of the cryoprobe may be flexible or rigid. In one embodiment the cryoprobe is a balloon catheter. The cryoprobe may be adapted to ablate, or carry out various therapies.

The shape and size of the thermally insulated containers may vary. In one embodiment the cryogenic container is a hand held size or mini-container with a protective insulating shell or cover. The insulation is removed and the containers are placed in a cooler or bath of the docking station to chill the liquid refrigerant to the predetermined cryogenic temperature. In another embodiment the containers are arranged in pairs in the form of a unit or cartridge. Each cartridge thus comprises a delivery container and a receiver cartridge. The cartridge is docked in the refrigerator and connected to the cryoablation apparatus as a unit during operation. In another embodiment the container is a single unit that is docked in the refrigerator and connected to the cryoablation apparatus as a single unit.

In another embodiment a cryoablation apparatus for treating tissue includes a cryoablation probe comprising a distal treatment section, a liquid refrigerant inlet line, and a liquid refrigerant return line. A first thermally insulated container for holding a liquid refrigerant is detachably coupled to the inlet line. A second thermally insulated container for holding the liquid refrigerant is detachably coupled to the return line. Liquid refrigerant is pumped from the first container, through the inlet line to the cryoprobe, and through the return line to the second container while remaining in a liquid state and without evaporation. In another embodiment, more than one cryoprobe can be connected to a single container using either a plurality of ports on the container, or a "splitter" junction on the liquid refrigerant inlet line leading to more than one cryoprobe.

In another embodiment, a method includes charging one or more thermally insulated containers with cold liquid refrigerant. Charging may be carried out by filling, cooling, or replenishing. One of the cryogenic containers is connected with the cryoprobe via an inlet line. The cryoablation probe is activated. Cold liquid refrigerant is pumped while the liquid refrigerant remains substantially at the predetermined cryogenic temperature to the cryoprobe tip where it is used for a cryosurgical procedure. The first container becomes substantially depleted of the liquid refrigerant. Next, the method includes detaching the first or delivery container from the cryoprobe and connecting a second chilled liquid refrigerant filled container to the inlet line of said cryoprobe.

The first container (which is now empty) or another empty container is then connected to a return line of the cryoprobe. It becomes a receiver container. The cryoprobe is activated wherein the chilled liquid refrigerant from the second container is delivered through the inlet line to the cryoprobe where the liquid refrigerant is warmed, and through the return line to the receiver container.

Driving the liquid refrigerant is carried out with a pump. In one embodiment pumping the liquid refrigerant is performed such that the liquid refrigerant remains in a single phase liquid state while being transported from the delivery container, through the cryoprobe, and to the receiver container.

In another embodiment, the method further comprises disconnecting the first container which was filled with warm return liquid and installing it in the docking station to be recharged.

In another embodiment the steps are repeated at least one time such that more than one container is charged, depleted, refilled, and recharged.

In another embodiment the charging is performed by removing insulation from the containers and placing the containers in a cooling medium. In another embodiment the charging is carried out by replenishing warm liquid refrigerant from the container with chilled liquid refrigerant from the docking station.

In another embodiment, one or more cartridges are provided which each include a delivery container and a receiver container. The cartridge is connectable as a unit to the cryoprobe or to the docking station.

In another embodiment the cryoprobe operates in an open loop configuration wherein the liquid refrigerant remains in a liquid state until it is transported downstream from the cryoprobe and is ejected into the atmosphere or elsewhere.

The description, objects and advantages of the present invention will become apparent from the detailed description to follow, together with the accompanying drawings.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

Figure 1:
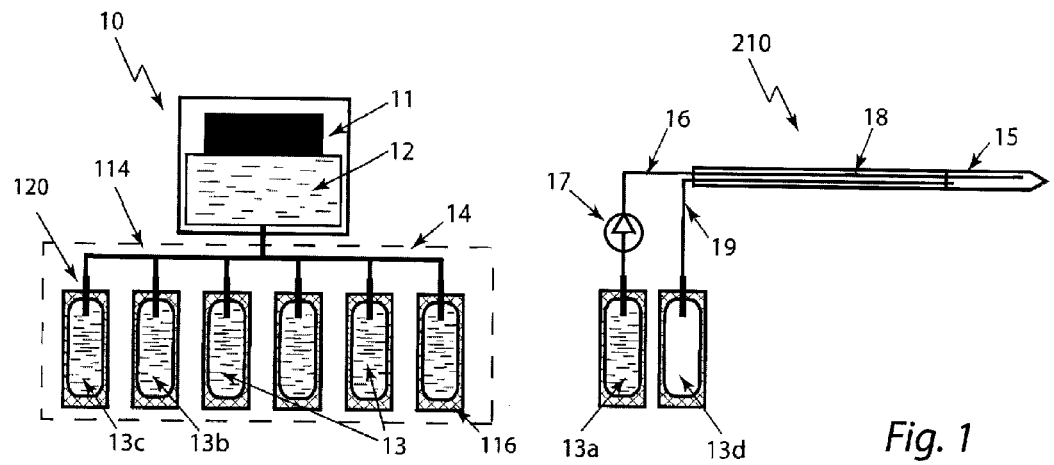
FIGS. 1-2 are schematic drawings illustrating a liquid refrigerant docking station and cryoprobe employing interchangeable liquid refrigerant containers.

Referring to FIG. 1, a cryoablation system 10 includes a refrigerator 11 with liquid refrigerant 12 at a predetermined cryogenic temperature (e.g. less than −100° C.) and a plurality of thermally insulated containers or canisters 13a,b,c,d. The containers 13c, 13b are shown docked in a docking station or chamber 14 of the refrigerator. The containers are shown having an insulation 116. The insulation 116 may be a vacuum shell or another type such as an insulative coating or removable cover or shell.

The containers 13 may be made of a wide variety of materials. Examples of suitable materials include, but are not limited to, stainless steel and aluminum. Additionally, the size of the containers may vary and a preferred shape is that of a hand-held cylindrical bottle (e.g., a 300 ml. water bottle). The volume of a container 13 may vary and range from 30 mL to 2000 mL. The volume of containers may correspond to the volume of liquid refrigerant required to carry out one procedure and perhaps as many as 10, and more preferably between 1-2 cryoablation procedures.

In the embodiment shown in FIG. 1, the refrigerator 11 holds and circulates the liquid refrigerant 12 to the containers 13c, 13b. The liquid refrigerant 12 is initially cooled and then delivered to the thermally insulated cryogenic containers. The refrigerator 11 replenishes or charges the liquid refrigerant 12 in the containers. Refrigerators such as, for example, a Pulse Tube Refrigerator (PTR) or Stirling cryocooler having a temperature regulating device can be used to cool the liquid refrigerant.

A preferred refrigerant is one that operates at low pressure, is commercially available, and is non-toxic. Non-limiting examples of liquid refrigerants suitable for use with the present invention are set forth in the TABLE below.

| Refrigerant | Chemical formula | Molecular mass (kg/mol) | Normal freezing point (° C.) |
| --- | --- | --- | --- |
| R124 | $C_2HClF_4$ | 136.5 | −199 |
| R218 | $C_3F_8$ | 188.02 | −150 |
| R290 | $C_3H_8$ | 44.1 | −188 |
| R1270 | $C_3H_6$ | 42.08 | −185 |
| R600A | $i-C_4H_{10}$ | 58.12 | −159.5 |

The liquid refrigerants shown above have varying properties. The liquid refrigerants, for example, have different boiling and freezing points. As such, and based on the viscosity and temperature/pressure parameters of a liquid refrigerant selected from the above TABLE, the system can be effectively customized to suit a particular cryosurgical procedure.

With reference to FIG. 1, the cold liquid refrigerant 12 is delivered to the thermally insulated cryogenic containers 13b, 13c placed in docking station which may be in the form of a chamber 14. The containers are fluidly connected to the refrigerator via one or more refrigerator lines 114. Each of the containers 13 has a connector 120 for detachably fluidly connecting to the refrigerator line 114. In one embodiment, line 114 includes two lumens: one lumen for fluid delivery and one lumen for fluid removal.

The line, however, may include more or less lumens. The lumens may serve various functions. The lumens, for example, may serve to deliver fresh chilled liquid, to remove warmer liquid, and to accommodate a temperature sensor or apparatus. Alternatively, separate lines may be provided to each container. The lines are fluidly connected to the container. An example of a connector is a fluid tight threaded nipple. However, other means of connectors may be used.

In one embodiment, a temperature sensor (e.g., a thermocouple) is inserted within one or more of the containers when the containers are docked. The temperature sensor can be incorporated into the refrigerator line such that it is positioned in the container when the line is connected to the container during docking. The temperature sensor measures the temperature of the liquid refrigerant within the container. The temperature signal is sent to the refrigerator for processing.

The refrigerator may include a programmable processor operable to receive the signal and adjust the liquid charging parameters. Examples of charging parameters include flowrate, temperature of the source refrigerant, and time. In this manner, chilled liquid refrigerant is delivered to the containers until the temperature of the liquid within the containers reaches a predetermined temperature.

FIG. 1 also shows a container 13a, 13d installed in fluid communication with the cryoprobe 210. In particular, inlet line 16 of the cryoprobe is fluidly connected to container 13a. A liquid pump 17 is positioned along the refrigerant flowpath to pressurize the liquid refrigerant, driving the liquid refrigerant from the container 13a to the cryoprobe tip section 15. In other embodiments the pump can be placed in other locations within the 210 system. Return line 19 transports the liquid refrigerant from the distal section 15 towards the proximal end of the probe and ultimately to an empty receiver container 13d.

FIG. 1 also shows cryoprobe having an insulation 18. The insulation 18 surrounds the inlet line 16 and return line 19 to thermally insulate them from causing thermal damage to the surrounding healthy tissues. Insulation 18 may be in the form of a vacuum shell or another type of insulation such as a coating having a low coefficient of thermal conductivity.

Figure 2:
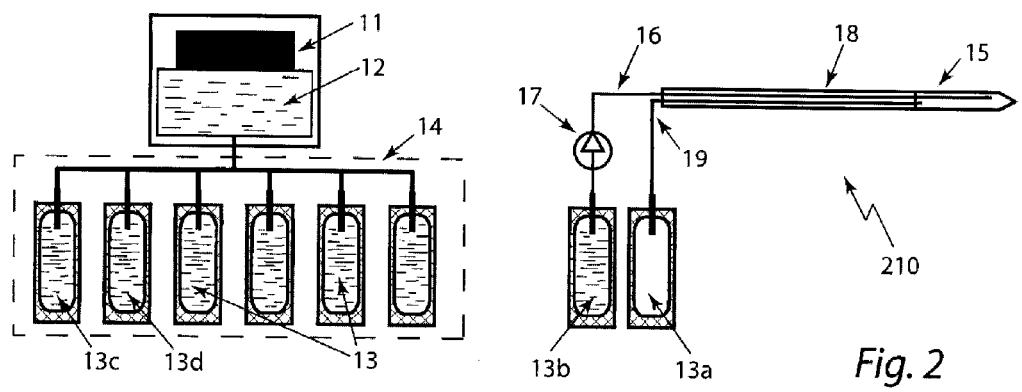

In a method of the present invention, and with reference to FIGS. 1-2, a liquid refrigerant 12 inside the thermally insulated cryogenic containers 13 is caused to reach a predetermined cryogenic temperature through use of a refrigerant 12 circulating in the refrigerator 11, and through refrigerator line 114 to the containers 13.

Next, a cryogenic container (e.g., 13a) is fluidly coupled to cryoprobe 210. The cryogenic delivery container 13a was previously charged in the chamber 14. Container 13a holds the liquid refrigerant 12 at the same predetermined cryogenic temperature as the refrigerator.

Next, cryoablation treatment is provided by circulating the pressurized cold liquid refrigerant from the cryogenic delivery container 13a through the cold inlet line 16, to cryoprobe tip 15. The liquid refrigerant is then directed through return line 19 into the empty receiver 13d. Empty receiver container 13d is designed the same as cryogenic containers 13a, 13b, 13c.

Next, the discharged cryogenic container 13a is disconnected from the inlet line 16 shown in FIG. 1 and connected to return line 19 of the cryoprobe 210 shown in FIG. 2. Container 13d, which has been filled with warmer discharged liquid refrigerant from the cryoprobe is placed or docked in chamber 14. Newly charged cryogenic container 13b is then connected with inlet line 16 and becomes a cryogenic delivery container as shown in FIG. 2.

In this manner, each of the containers 13a,b,c,d may be charged, spent (or used), refilled, and returned to the docking station in a convenient, interchangeable manner. The containers shown in this embodiment are identical in shape and size.

Figure 3:
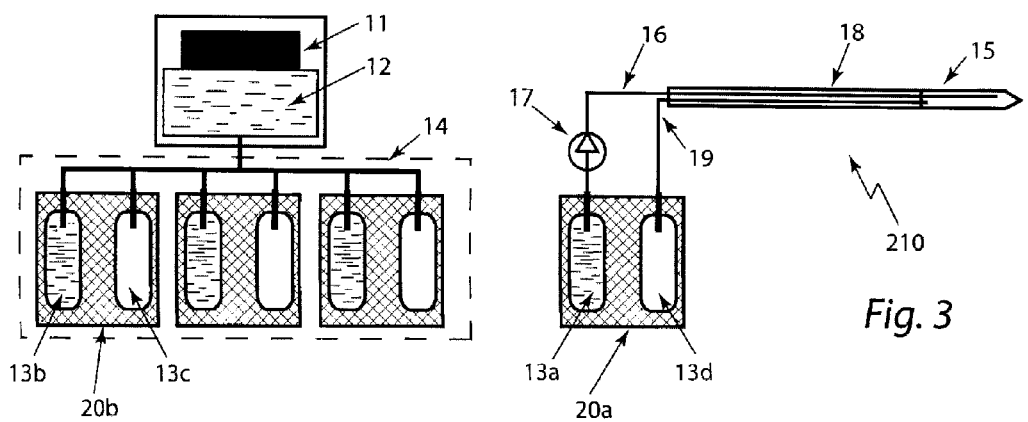
FIGS. 3-4 are schematic drawings illustrating a liquid refrigerant docking station and cryoprobe employing interchangeable liquid refrigerant cartridges.

FIG. 3 illustrates another embodiment of the present invention. In particular, cartridge 20a includes a liquid delivery container (e.g., 13a) and receiver container (e.g., 13d). Cartridge 20a is an integrated unit. Cartridge 20 may be docked in the docking station to be charged with liquid refrigerant and subsequently connected to cryoprobe 210 as a unit.

Figure 4:
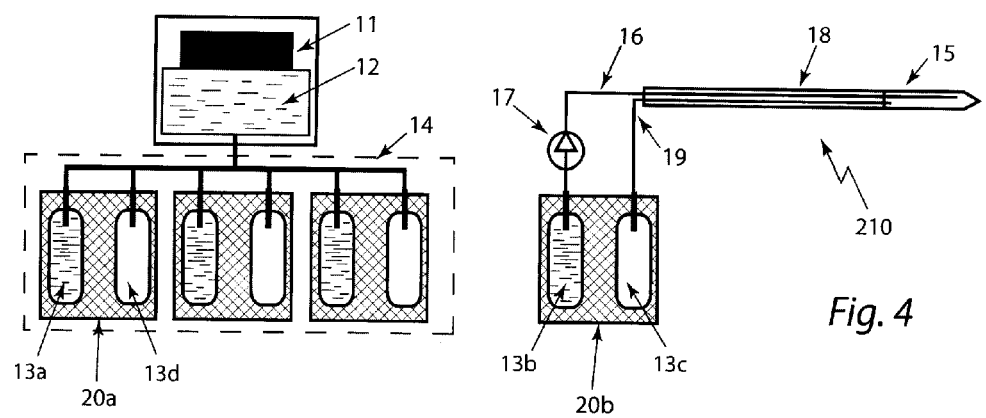

In operation, and as shown in FIG. 3, Cartridge 20a is connected with cryoprobe 210. Liquid refrigerant is transported from delivery container or canister 13a, through cryoprobe 210, and back to receiver container 13d. Next, cartridge 20a is disconnected from the cryoprobe 210 and pre-charged cartridge 20b is connected to cryoprobe 210 as shown in FIG. 4. Cartridge 20a may be docked in docking station 14 to be recharged.

In this embodiment, the cartridges 20 are conveniently connected and removed from the docking system and cryoprobe as units.

Figure 5:
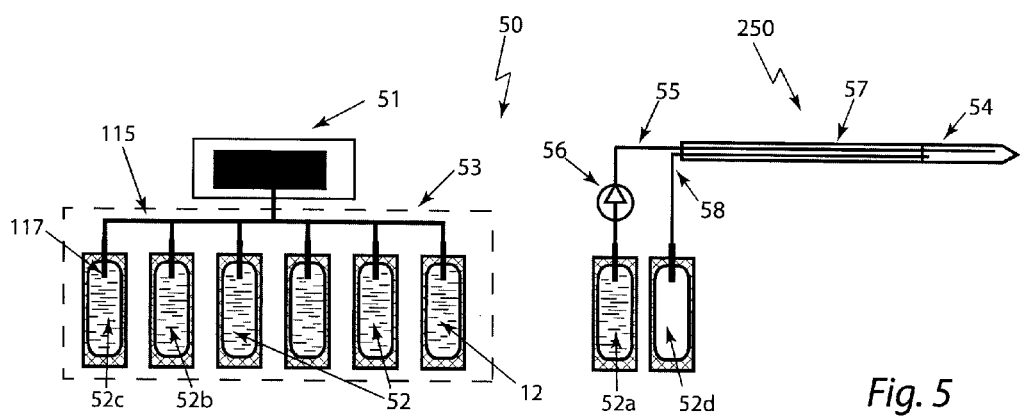
FIGS. 5-6 are schematic drawings illustrating another liquid refrigerant docking station and cryoprobe employing interchangeable liquid refrigerant containers.
Figure 6:
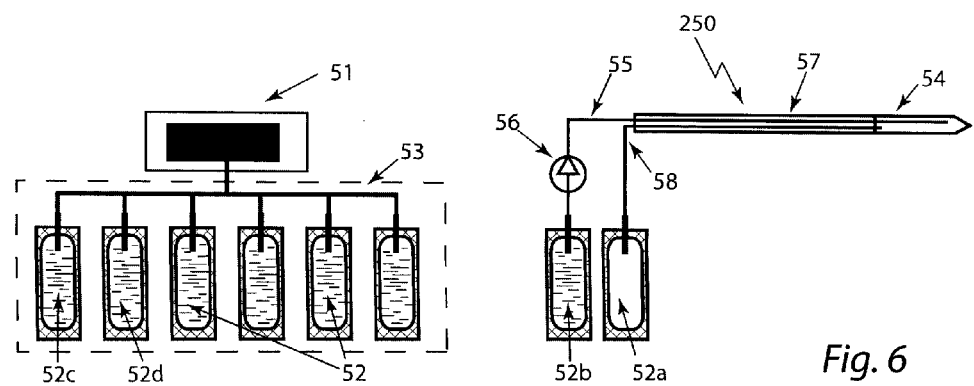

FIGS. 5-6 illustrate another embodiment of the present invention. The embodiment shown in FIGS. 5-6 is similar to that described in FIGS. 1-2 except that refrigerator 51 cools the liquid refrigerant 12 inside the thermally insulated cryogenic containers 52 to reach a predetermined cryogenic temperature (e.g. less than −100° C.) rather than replaces or replenishes it. FIGS. 5-6 show a refrigerating element 117 positioned in the containers 52 while the containers are docked. The refrigerator element 117 conducts thermal energy to the liquid 12 inside the containers 52 thereby cooling the liquid to the desired cryogenic temperature.

The refrigerator element 117 may have a various configurations. In one variation the refrigerator element 117 is a closed-loop cooling element in which an intermediate refrigerant flows there through to deliver thermal energy to the liquid refrigerant 12 within the containers 52. In another embodiment the refrigerator element 117 is a thermally conductive material (e.g., a finger) that transfers thermal energy from the refrigerator source directly to the liquid within the docked containers.

In another embodiment, the insulation of the containers is removed and the containers are placed in a cooling medium of the docking station 53. The cryobath causes the liquid refrigerant 12 within the containers 52 to cool to the desired temperature. The insulation may then be put back in place prior to connecting the containers with the cryoprobe FIG. 5 also illustrates one of the thermally insulated cryogenic containers 52a connected with cold inlet line 55 of cryoprobe 250. Although not shown, this container 52a was previously charged in chamber 53.

The cryogenic delivery container 52a is shown installed in fluid communication with the cryoprobe 250. Liquid pump 56 pressurizes the liquid refrigerant 12 driving the liquid from delivery container 52a to the cryoprobe tip section 54.

A cold inlet line 55 extends through the vacuum shell 57 from the proximal end of the cryoprobe to its distal end. The vacuum shell 57 is provided to thermally insulate the cold inlet liquid line 55 from the surrounding healthy tissues. Similarly, a return line 58 extends proximally from the cryoprobe tip section 54, back through the vacuum shell 57 to establish fluid communication between the cryoprobe tip section 54 and empty receiver 52d. Though a vacuum shell 57 is shown in this embodiment, the invention contemplates use of other types of insulation. Additionally, the containers 52 in this embodiment are shown as being identical and conveniently interchangeable.

In a method of the present invention, and with reference to FIGS. 5-6, a liquid refrigerant 12 inside the thermally insulated cryogenic containers 52 is cooled to a predetermined cryogenic temperature by a refrigerator 51, and through refrigerator line element 117. Element 117 is shown inserted in each of the containers in the docking station 53.

Next, Cryogenic container 52a is fluidly coupled to cryoprobe 250. The cryogenic delivery container 52a was previously charged in the chamber 53. Container 52a holds the liquid refrigerant 12 at the same predetermined cryogenic temperature as the refrigerator.

Next, cryoablation treatment is provided by circulating the pressurized cold liquid refrigerant from the cryogenic delivery container 52a through the cold inlet line 55 to cryoprobe tip 54. The discharged liquid refrigerant is then directed through return line 58 to empty receiver 52d.

Next, and with reference to FIG. 6, the discharged cryogenic container 52a is disconnected from the inlet line 55 and connected to return line 58 of the cryoprobe 250. Container 52d, which has been filled with warmer liquid from the cryoprobe 250 is placed or docked in chamber 53. Newly charged cryogenic container 52b is then connected with inlet line 55 and becomes a cryogenic delivery container as shown in FIG. 6.

In this manner, each of the containers 52a,b,c,d may be charged, used in the procedure, refilled, and returned to the docking station in a convenient, interchangeable manner. The containers shown in this embodiment are identical in shape and size.

Figure 7:
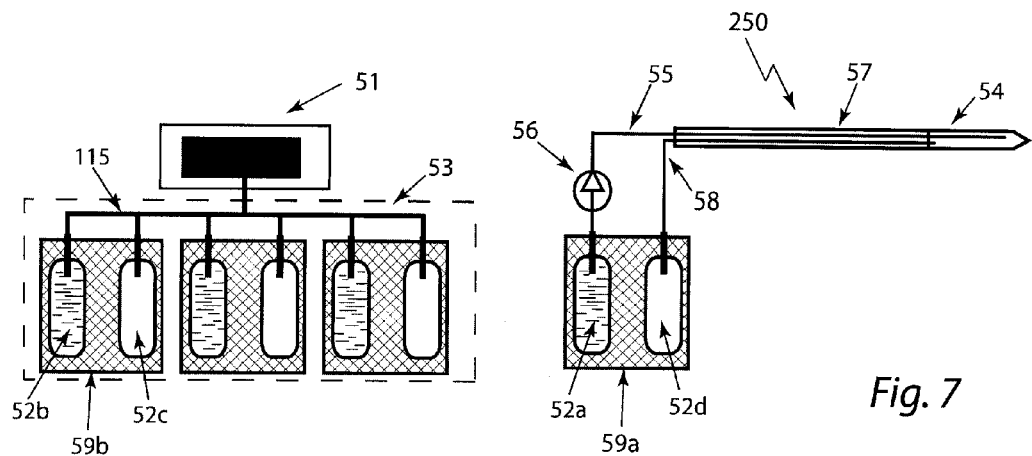
FIGS. 7-8 are schematic drawings illustrating another liquid refrigerant docking station and cryoprobe employing interchangeable liquid refrigerant cartridges.

FIG. 7 illustrates another embodiment of the present invention. In particular, a cartridge 59a is shown having two components (liquid delivery container 52a and receiver container 52d) which cooperate together as an integrated unit. Cartridge 59 is docked in the docking station 53 to be charged with liquid refrigerant and subsequently connected to cryoprobe 250 as a unit.

Figure 8:
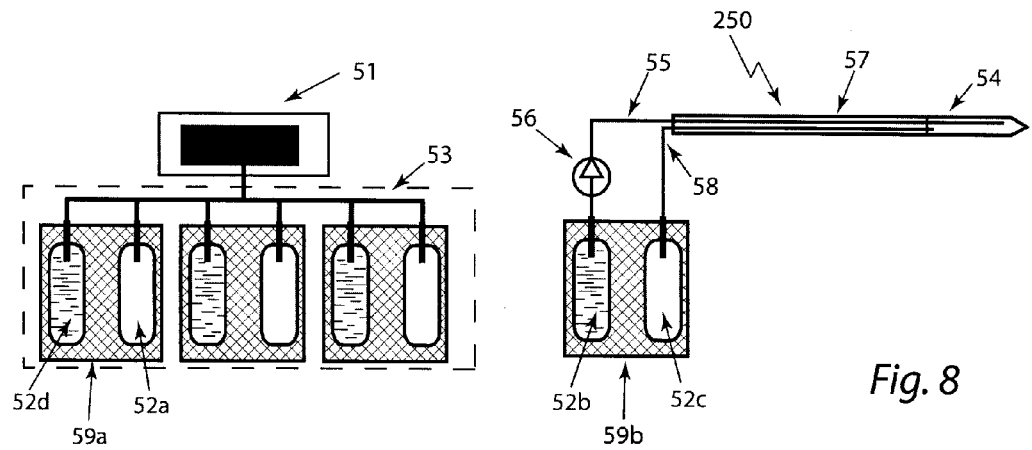

In operation, and as shown in FIG. 7, liquid refrigerant 12 is transported from delivery container or canister 52a, through cryoprobe 250, and back to receiver container 52d. Next, cartridge 52a is disconnected from the cryoprobe 250 and pre-charged cartridge 59b is connected to cryoprobe 250 as shown in FIG. 8. Cartridge 59a may be installed in docking station 53 to be recharged. The cartridges 59 are thus conveniently connected and removed from the docking system and cryoprobe as units.

Figure 9:
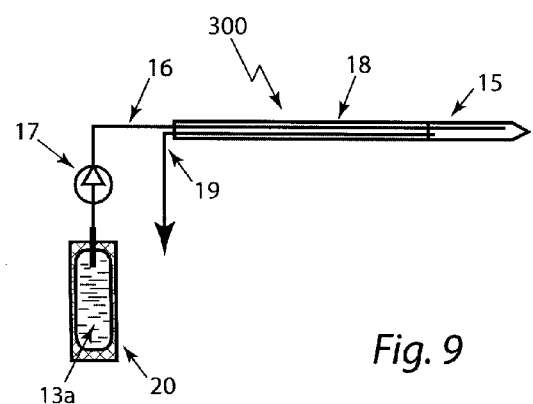
FIG. 9 is a schematic drawing illustrating a liquid refrigerant cryoprobe employing an interchangeable liquid refrigerant container in an open cycle cryosurgical operation.

FIG. 9 illustrates another embodiment of the present invention. The cryoprobe 300 shown in FIG. 9 is an open cooling cycle cryosurgical operation. In particular, a cryoprobe is shown connected with container 13a via inlet line 16. The liquid refrigerant is transported to the distal tip section 15. However, in this embodiment, the liquid refrigerant 12 is freely discharged or ejected into the atmosphere through return line 19 instead of being collected in a discharge container as described above.

It should also be understood that the cryoprobe described above may vary widely and include, for example, a catheter or rigid instrument for applying thermal energy. The cryoprobe may comprise inflatable or expanding regions carried out by balloons or other types of expanding means. The cryoprobe may ablate tissue by applying cryoenergy to the tissue. The cryoprobe may comprises a freeze zone along the distal section or be confined to the tip. The cryoprobe may also include pull wires or other means to effectuate curvature.

While the disclosed cooling system for cryoablation treatment as herein shown in detail is fully capable of obtaining the objects and providing the advantages herein before stated, it is to be understood that is merely illustrative of the presently preferred embodiment of the invention and that no limitations are intended to the details of construction or design herein shown other than as described in the appended claims.

We claim:

1. A cryoablation system for a treatment of biological tissues, said system comprising:
    a cryoablation probe and an inlet line extending from a proximal end of the cryoablation probe;
    a plurality of containers, each of said plurality of containers being portable and thermally insulated, the plurality of containers are configured for holding a liquid refrigerant;
    a refrigerator comprising
        a container docking station, said docking station comprising a chamber adapted to removably receive said plurality of containers when the cryoablation probe is not connected to the containers, and for cooling said liquid refrigerant contained within said plurality of containers when said plurality of containers are docked in said station and wherein each of said plurality of containers comprises a connector adapted to removably connect to the inlet line of the cryoablation probe such that when the cryoablation probe is connected with a first container of said plurality of containers positioned outside of the refrigerator and is filled with cooled liquid refrigerant, the liquid refrigerant is transported from said first container through the inlet line and to the cryoablation probe; and wherein said refrigerator further comprises a refrigerant element placed in direct contact with said liquid refrigerant within each container of said plurality of containers when said plurality of containers are docked such that said refrigerant element transfers thermal energy to said liquid refrigerant in each container of said plurality of containers.

2. The system of claim 1 wherein the refrigerator element comprises a thermally conductive finger that transfers thermal energy to the liquid refrigerant.

3. The system of claim 2 wherein each of said plurality of containers comprise removable insulation.

4. The system of claim 3 wherein said docking station is a cooling chamber.

5. The system of claim 1 wherein said refrigerator comprises a charging line which is fluidly connectable to one of said plurality of containers when said one container is placed in the docking station such that said one container may be replenished with liquid refrigerant at a cryogenic temperature.

6. The system of claim 1 further comprising the liquid refrigerant under low pressure.

7. The system of claim 6 further comprising a liquid pump disposed along a flowpath of the liquid refrigerant.

8. The system of claim 7 further comprising a return line along said liquid refrigerant flowpath, said return line directing the liquid refrigerant away from the cryoablation probe.

9. The system of claim 8 wherein said return line is detachably connectable to the connector such that the cryoablation probe may be connected to the first container via the inlet line and a second container of said plurality of containers via the return line simultaneously.

10. The system of claim 9 wherein the inlet line, the pump, the cryoablation probe, and the return line operate to maintain the liquid refrigerant in a single phase liquid state along the flowpath.

11. The system of claim 10 wherein said first container and said second container form a cartridge.

12. The system of claim 6 wherein the cryoablation probe is flexible.

13. The system of claim 12 wherein the cryoablation probe is a balloon catheter.

14. The system of claim 6 wherein the cryoablation probe is rigid.

15. The system of claim 1 wherein said liquid refrigerant is selected from a group consisting of $C_2HClF_4$, $C_3F_8$, $C_3H_8$, $C_3H_6$, and i-$C_4H_{10}$.

16. The system of claim 1 wherein each of the plurality of containers is hand-held sized.

17. A cryoablation apparatus for treating living tissue comprising:
  a cryoablation probe comprising a distal treatment section, a liquid refrigerant inlet line, and a liquid refrigerant return line;
  a portable first thermally insulated container for holding a liquid refrigerant, said first container detachably coupled to said inlet line; and
  a portable second thermally insulated container for holding the liquid refrigerant, said second container detachably coupled to said return line whereby said liquid refrigerant is configured to be pumped from said first container, through said inlet line to said cryoablation probe, and through said return line to said second container while remaining in a liquid state and without evaporation while treating living tissue, wherein said first container and said second container are each sized to hold a volume of the liquid refrigerant of between 30 ml and 2000 ml. when filled.

18. The cryoablation apparatus of 17 wherein said cryoablation probe includes an evacuated space surrounding the inlet line.

19. The cryoablation apparatus of 17 wherein said cryoablation probe further comprises a liquid pump.

20. The cryoablation apparatus of 17 wherein said cryoablation probe comprises a rigid shaft.

21. The cryoablation apparatus of claim 17 wherein said first container and said second container cooperate together as an integral cartridge that is connectable as a single unit to the cryoablation probe and wherein the first container defines a first discrete enclosed volume and the second container defines a second discrete enclosed volume.

22. The cryoablation apparatus of 17 wherein said cryoablation probe comprises a flexible catheter.

23. The cryoablation apparatus of claim 17 wherein the first thermally insulated container comprises a removable insulative shell.

24. The cryoablation apparatus of claim 17 wherein each of the first thermally insulated container and the second thermally insulative container is hand-held sized.

25. A cryoablation system for a treatment of biological tissues, said system comprising:
  a plurality of containers, each of said plurality of containers being small, portable and thermally insulated, and each of the plurality of containers further being configured to detachably connect to a cryoablation probe such that a liquid refrigerant contained within an attached container may be transported to the cryoablation probe during the treatment; and
  a docking station comprising
    a chamber adapted to receive the plurality of containers when the cryoablation probe is separated from the plurality of containers, and for cooling said liquid refrigerant contained within said plurality of containers when said plurality of containers are docked therein whereby said cooling is carried out without refilling said plurality of containers, and
    a plurality of refrigerator elements, each of said refrigerator elements insertable into the liquid refrigerant contained within each of the containers and for conducting thermal energy to said liquid refrigerant to lower the liquid refrigerant temperature to a cryogenic temperature.

26. A cryoablation system for a treatment of biological tissues, said system comprising:
  a plurality of containers, each of said plurality of containers being small, portable and thermally insulated, and each of the plurality of containers further being configured to detachably connect to a cryoablation probe such that a liquid refrigerant contained within an attached container may be transported to the cryoablation probe during the treatment; and
  a docking station comprising a chamber adapted to receive the plurality of containers when the cryoablation probe is separated from the plurality of containers, and for cooling said liquid refrigerant contained within said plurality of containers when said plurality of containers are docked therein whereby said cooling is carried out by evacuating said liquid refrigerant from each of the containers to create a space, and filling the space with a chilled liquid refrigerant.

27. The system of claim 26, further comprising a multilumen refrigerator line to connect to each of the containers, said multilumen line comprising an outlet lumen and an inlet lumen for evacuation and filling liquid refrigerant respectively.

* * * * *